US012564466B2

(12) United States Patent (10) Patent No.: US 12,564,466 B2
Xodo et al. (45) Date of Patent: Mar. 3, 2026

(54) CONTAINER AND KIT FOR WASHING AND/OR DISINFECTING AND/OR STERILISING MEDICAL INSTRUMENTS

(71) Applicant: GEM S.N.C. DI ENRICO XODO E GUIDO CAPPELLINA, Padua (IT)

(72) Inventors: Enrico Xodo, Padua (IT); Guido Cappellina, Padua (IT)

(73) Assignee: GEM S.N.C. DI ENRICO XODO E GUIDO CAPPELLINA, Padua (IT)

( * ) Notice: Subject to any disclaimer, the term of this patent is extended or adjusted under 35 U.S.C. 154(b) by 0 days.

(21) Appl. No.: 18/693,423

(22) PCT Filed: Aug. 26, 2022

(86) PCT No.: PCT/IB2022/057996
§ 371 (c)(1),
(2) Date: Mar. 19, 2024

(87) PCT Pub. No.: WO2023/042017
PCT Pub. Date: Mar. 23, 2023

(65) Prior Publication Data
US 2024/0390096 A1 Nov. 28, 2024

(30) Foreign Application Priority Data

Sep. 20, 2021 (IT) ........................ 102021000024095

(51) Int. Cl.
*A61B 50/33* (2016.01)
*A61B 90/70* (2016.01)
(Continued)

(52) U.S. Cl.
CPC .............. *A61B 50/33* (2016.02); *A61B 90/70* (2016.02); *A61L 2/26* (2013.01); *B08B 3/04* (2013.01);
(Continued)

(58) Field of Classification Search
CPC ......... A61B 50/33; A61B 50/22; A61B 50/34; A61B 2050/005; B65D 1/38; B65D 21/0233
(Continued)

(56) References Cited

U.S. PATENT DOCUMENTS 5,540,901 A * 7/1996 Riley ...................... A61B 50/22
206/370
5,732,821 A * 3/1998 Stone ...................... A61B 50/30
206/439
(Continued)

FOREIGN PATENT DOCUMENTS

DE 202009012909 U1 2/2011
DE 102010050919 A1 5/2012
(Continued)

OTHER PUBLICATIONS

European Patent Office, International Search Report and Written Opinion for PCT Application Serial No. PCT/IB2022/057996, Nov. 23, 2022, 11 pages.

*Primary Examiner* — Robert Poon
(74) *Attorney, Agent, or Firm* — FERENCE & ASSOCIATES LLC

(57) ABSTRACT

Container (1) and kit for washing and/or disinfecting and/or sterilising medical instruments comprising a frame (10), made of a polymeric material and defining a containment volume (V) and a plurality of containment panels (20), made of a metal material, constrained or constrainable to the frame (10) and defining a bottom wall (21), an upper wall (22) and a plurality of side walls (23, 24, 25, 26) of the container (1) so as to delimit the containment volume (V). Furthermore, the containment panels (20) have a plurality of holes suitable for the passage of a washing fluid. Not least, the containment panels (20) have a planar shape.

12 Claims, 6 Drawing Sheets

(51) Int. Cl.
    *A61L 2/26*       (2006.01)
    *B08B 3/04*       (2006.01)

(52) U.S. Cl.
    CPC ....... *A61L 2202/17* (2013.01); *A61L 2202/24* (2013.01)

(58) Field of Classification Search
    USPC ........................................ 206/370; 220/23.88
    See application file for complete search history.

(56)                References Cited

U.S. PATENT DOCUMENTS

| | | | | |
|---|---|---|---|---|
| 5,913,422 | A * | 6/1999 | Cote | A61L 2/26 206/370 |
| 6,099,812 | A * | 8/2000 | Allen | A61L 2/26 206/370 |
| 6,365,115 | B1 | 4/2002 | Wood | |
| 6,783,004 | B1 * | 8/2004 | Rinner | A61B 17/8875 206/370 |
| 6,783,044 | B2 * | 8/2004 | Perra | B25C 1/008 227/8 |
| 2013/0334083 | A1 * | 12/2013 | Bugnard | A61B 50/30 206/370 |
| 2014/0069841 | A1 * | 3/2014 | Pizzato | B25H 3/026 206/570 |
| 2014/0158570 | A1 | 6/2014 | Cushion et al. | |
| 2016/0367370 | A1 * | 12/2016 | Kim | A61B 50/30 |
| 2018/0271632 | A1 * | 9/2018 | Berg | A61B 50/20 |
| 2021/0244842 | A1 * | 8/2021 | Gillstrap | A61B 50/33 |
| 2021/0386499 | A1 * | 12/2021 | Bailey | A61B 50/33 |

FOREIGN PATENT DOCUMENTS

| | | |
|---|---|---|
| WO | WO2014188348 A1 | 11/2014 |
| WO | WO2016208956 A1 | 12/2016 |
| WO | WO2018022146 A1 | 2/2018 |
| WO | WO2019197494 A1 | 10/2019 |

* cited by examiner

CONTAINER AND KIT FOR WASHING AND/OR DISINFECTING AND/OR STERILISING MEDICAL INSTRUMENTS

The present application is a National Phase Entry of PCT International Application No. PCT/IB2022/057996, which was filed on Aug. 26, 2022, which claims priority to Italian Application No. 102021000024095, which was filed on Sep. 20, 2021, the contents of both of which are hereby incorporated by reference.

TECHNICAL FIELD

The present invention relates to a container for washing (manual or automatic) and/or disinfecting (manual or automatic) and/or for sterilising (manual or automatic) medical instruments and a kit for washing and/or disinfecting and/or sterilising medical instruments comprising such a container.

In general, the present invention finds application in the medical and healthcare fields. In particular, the present invention is preferably used in the dental field.

BACKGROUND OF THE INVENTION

In such fields, it is often necessary to have containers for washing and/or disinfecting and/or sterilising within which a support tray and/or clipper are arranged, onto which the medical instruments are positioned. In particular, the support trays and clippers, solidly constrained in use to the container, allow the instruments to be retained and attached inside the container during the washing and/or disinfecting and/or sterilising steps. In addition, the support trays and clippers allow, after washing, to provide (preferably "within reach") the doctor with the tools necessary to perform predefined operations.

In particular, in the dental field, various types of instruments must be made available to the doctor. In practice, the support tray and/or clippers retain the instruments that the dentist deems appropriate to have available. In any case, the present invention is part of what is commonly called: "surgical kit".

Functionally, following the insertion of the instruments, the containers are arranged in cleaners for washing and/or disinfecting and/or sterilising. Such cleaners operate by means of a washing fluid, typically only water or water mixed with one or more solvents. Preferably, such cleaners are defined by a special type of dishwasher called "thermal washer disinfectors".

Alternatively, such cleaners can be of the ultrasonic type. In particular, ultrasonic cleaning is a process that uses ultrasound to stir the washing fluid so as to wash and sanitise the medical instruments more effectively. From a constitutive point of view, a container of a type known in the technical field pertaining to the present invention essentially comprises a containment body defining a substantially parallelepiped-shaped containment volume.

The containment body comprises one or more components of polymeric material and/or one or more components of metal material.

Typically, the frame is mostly made of polymeric material and/or metal material while the walls of the container, perforated so as to allow the passage of the washing fluid, are made of metal material.

Nevertheless, although widely used, even in their most modern implementations and while having significantly eliminated or reduced some disadvantages, the known type of containers still have some structural, operational and economic/productive disadvantages which make their use not without problems.

Firstly, the structure of the container is considerably complex and, consequently, expensive in economic/productive terms.

In fact, the metal components, especially in the connection portions, have a particularly complex shape that requires expensive moulding and deformation processes during production.

A further problem concerns the lack of versatility of the support trays and/or clippers, inadequate to adapt to a plurality of operating conditions. Moreover, a further problem concerns the materials with which the support trays and/or clippers are made that do not allow an efficient and deep washing of the medical instruments.

OBJECTS OF THE PRESENT INVENTION

In such a context, the technical task of the present invention is therefore to provide a container for washing and/or disinfecting and/or sterilising medical instruments as well as a kit for sanitising medical instruments comprising such a container which are free from the drawbacks which have emerged from the prior art.

Not least, an object of the present invention is to provide a container for washing and/or disinfecting and/or sterilising medical instruments as well as a kit for sanitising medical instruments which are capable of being simple, robust and inexpensive.

A further object of the present invention is to provide a container for washing and/or disinfecting and/or sterilising medical instruments as well as a kit for sanitising medical instruments which are capable of being extremely versatile.

Moreover, an object of the present invention is to provide a container for washing and/or disinfecting and/or sterilising medical instruments as well as a kit for sanitising medical instruments capable of being particularly efficient and ensuring a deep cleaning of the instruments.

The specified technical task and the specified objects are fully achieved by a container for sanitising medical instruments as well as a kit for sanitising medical instruments comprising such a container which is the object of the present invention, which are characterised by what is contained in the accompanying claims.

The features and advantages of the present invention will become more apparent from the detailed description of some preferred, non-exclusive embodiments of a container for sanitising medical instruments and a kit for sanitising medical instruments in accordance with the present invention.

BRIEF DESCRIPTION OF THE FIGURES

Such a description will be set out below with reference to the appended drawings, which are provided solely for illustrative and therefore non-limiting purposes, in which.

DESCRIPTION OF ONE OR MORE PREFERRED EMBODIMENTS OF THE PRESENT INVENTION

Figure 1:
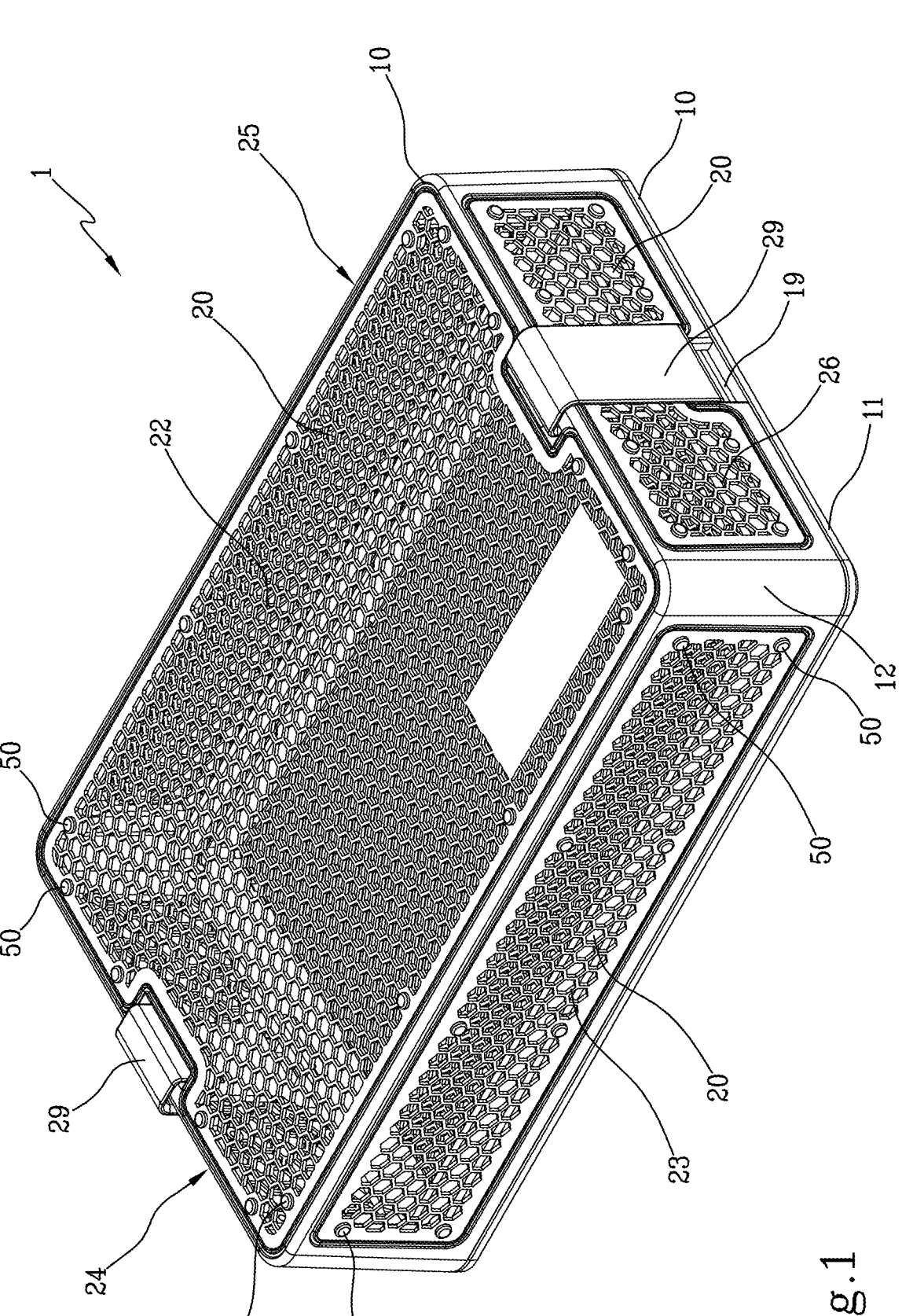
FIG. 1 shows a schematic view of a first embodiment (exemplary but non-limiting) of a container for sanitising medical instruments in accordance with the present invention in a closing configuration.

With reference to the appended drawings, the kit for sanitising medical instruments which is the object of the present invention comprises a container for sanitising medical instruments, indicated in the drawings with the numerical reference "1", and at least one instrument support tray indicated with the numerical reference "30".

Structurally, the container 1 comprises a frame 10 defining a containment volume "V" and a plurality of containment panels 20 constrained or constrainable to the frame 10 and defining a bottom wall 21, an upper wall 22 and a plurality of side walls 23, 24, 25, 26 of the container 1 so as to delimit the containment volume "V".

By way of non-limiting example, a preferred embodiment of the container 1 is illustrated in the appended drawings.

In such an embodiment, the containment volume "V" has a substantially parallelepiped shape. In particular, the containment panels 20 define four side walls 23, 24, 25, 26.

Alternatively, the containment volume "V" can have a cubic shape.

The frame 10 is defined (preferably only) by the segments defining the sides of a rectangular or square parallelepiped.

The frame 10 is made of a polymeric material. Preferably, the frame 10 is made of plastic. Even more preferably, the frame 10 is made of PPSU plastic (Polyphenylsulfone).

Advantageously, such a material ensures high hydrolytic stability. Furthermore, such a material has a considerable hardness and a high resistance to heat, especially at high temperatures and even after repeated washing and/or sterilisation cycles while maintaining its aesthetic features substantially unchanged.

The containment panels 20 are instead made of a metal material. Preferably, the containment panels 20 are made of steel. Even more preferably, the containment panels 20 are made of stainless steel.

Structurally, the containment panels 20 have a plurality of holes suitable for the passage of a washing fluid.

In the present description, the term "washing fluid" can mean only water, as well as water mixed with a solvent.

The holes can have any shape, size and/or arrangement as long as they allow the correct passage of the washing fluid through the containment panels 20 and therefore a correct washing and a correct sanitisation of the medical instruments arranged inside the container 1.

Preferably, the holes have a hexagonal shape, but can also have other shapes such as, for example, circular or square or anything else not expressly mentioned herein.

Preferably, such holes are made so as to define a high ratio between the passage area and the metal surface in order to facilitate and make the cleaning and/or disinfecting and/or sterilising more efficient.

According to a further aspect, each covering panel 20 defines a respective container wall of the aforesaid bottom walls 21, upper wall 22 and side walls 23, 24, 25, 26.

According to a preferable aspect of the present invention, the containment panels 20 have a planar shape.

Advantageously, such a technical feature ensures a remarkably efficient production in terms of costs and time of the metal components. It follows that, overall, the production of the container 1 is also convenient from the production point of view.

In fact, the more structurally complex components, for example those for connection, are comprised in the frame 10 and are thus made of polymeric material, easily and conveniently mouldable.

The containment panels 20 are attachable or attached to the frame 10 by attachment means.

Preferably, the containment panels 20 have attachment holes 50 engageable by pegs (which are integral with the frame 10) for a snap coupling, shape coupling and/or by means of welding the pegs themselves.

Alternatively, the attachment holes 50 of the containment panels 20 can be engaged by respective threaded members and reversibly constrained to the frame 10 by such threaded members.

Figure 3:
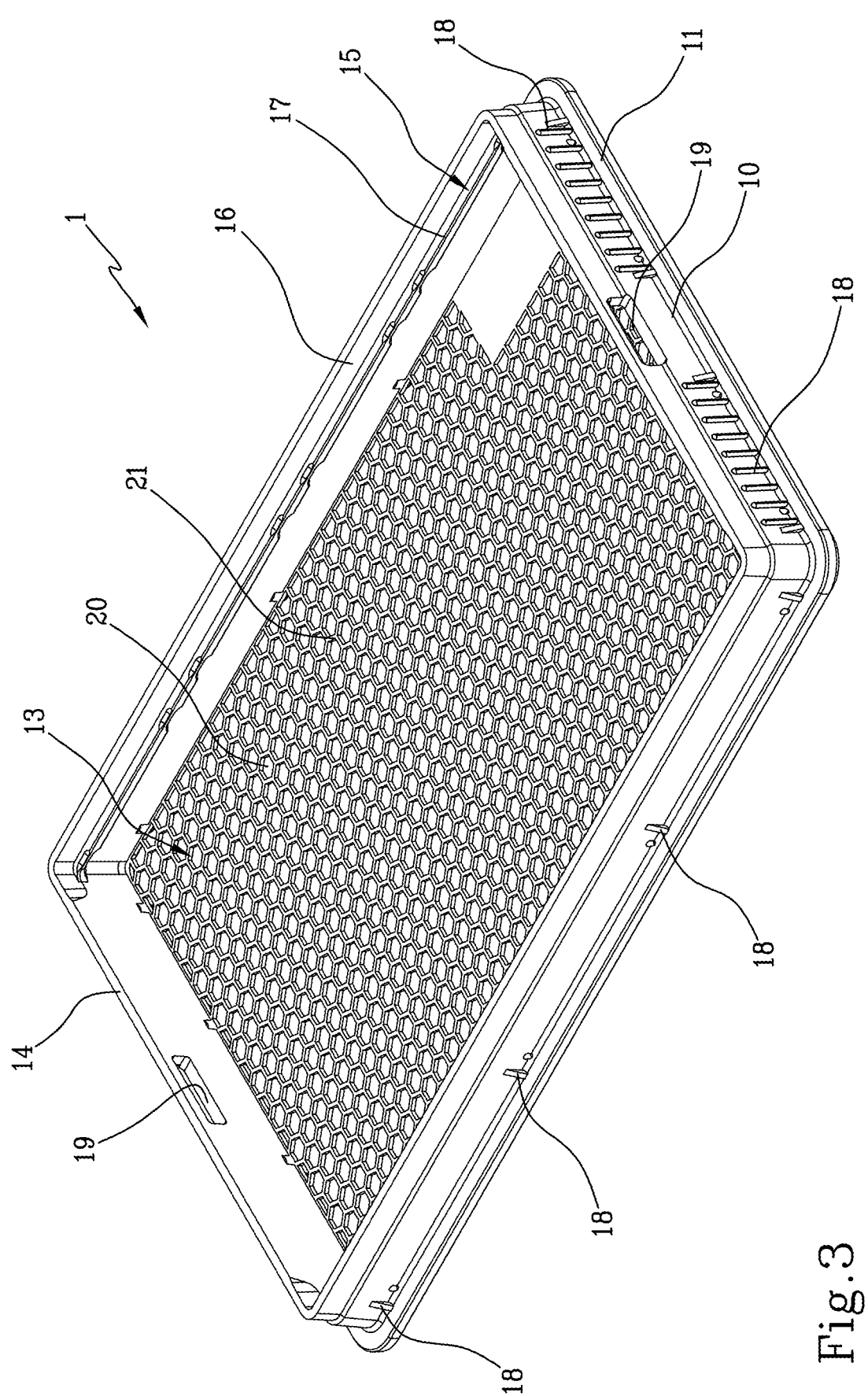
FIG. 3 shows a schematic view of a component of the container of FIG. 1.

According to a further aspect of the present invention, the frame 10 can comprise a base element 11, illustrated in FIG. 3, adapted to define a housing seat 13 for one or more instrument support trays 30, and a covering element 12, that can be reversibly coupled to the base element 11 by means of a shape coupling and configured to at least partially cover the base element 11 in a closing configuration of the container 1.

In such an embodiment, the bottom wall 21 of the container 1 is solidly constrained to the base element 11 while the side walls 23, 24, 25, 26 and the upper wall 22 are solidly constrained to the covering element 12. Moreover, in the closing configuration of the container 1, the base element 11 is at least partially inserted inside the covering element 12.

According to a further structural aspect, the base element 11 and the covering element 12 can comprise reversible mutual coupling means 19, 29 configured to determine a stable attachment of the base element 11 to the covering element 12.

In particular, the base element 11 can have coupling seats 19 while the covering element 12 can comprise tilting hooks 29 engageable in the coupling seats 12 so as to define a stable clamping of the base element 11 to the covering element 12.

Preferably, the base element 11 comprises a pair of coupling seats 19 made on opposite walls of the base element 11 while the covering element 12 comprises a pair of tilting hooks 29 made on respective opposite walls of the covering element 12, for example the side walls 24, 26.

Advantageously, such a technical feature allows an extremely solid and reliable closing configuration of the container 1, especially in the washing steps of the container 1.

According to a further structural aspect, furthermore, the base element 11 and the covering element 12 can comprise guide elements 18 counter-shaped to each other and adapted to define a unique mutual positioning between the base element 11 and the covering element 12 in the closing configuration of the container 1.

Figure 2:
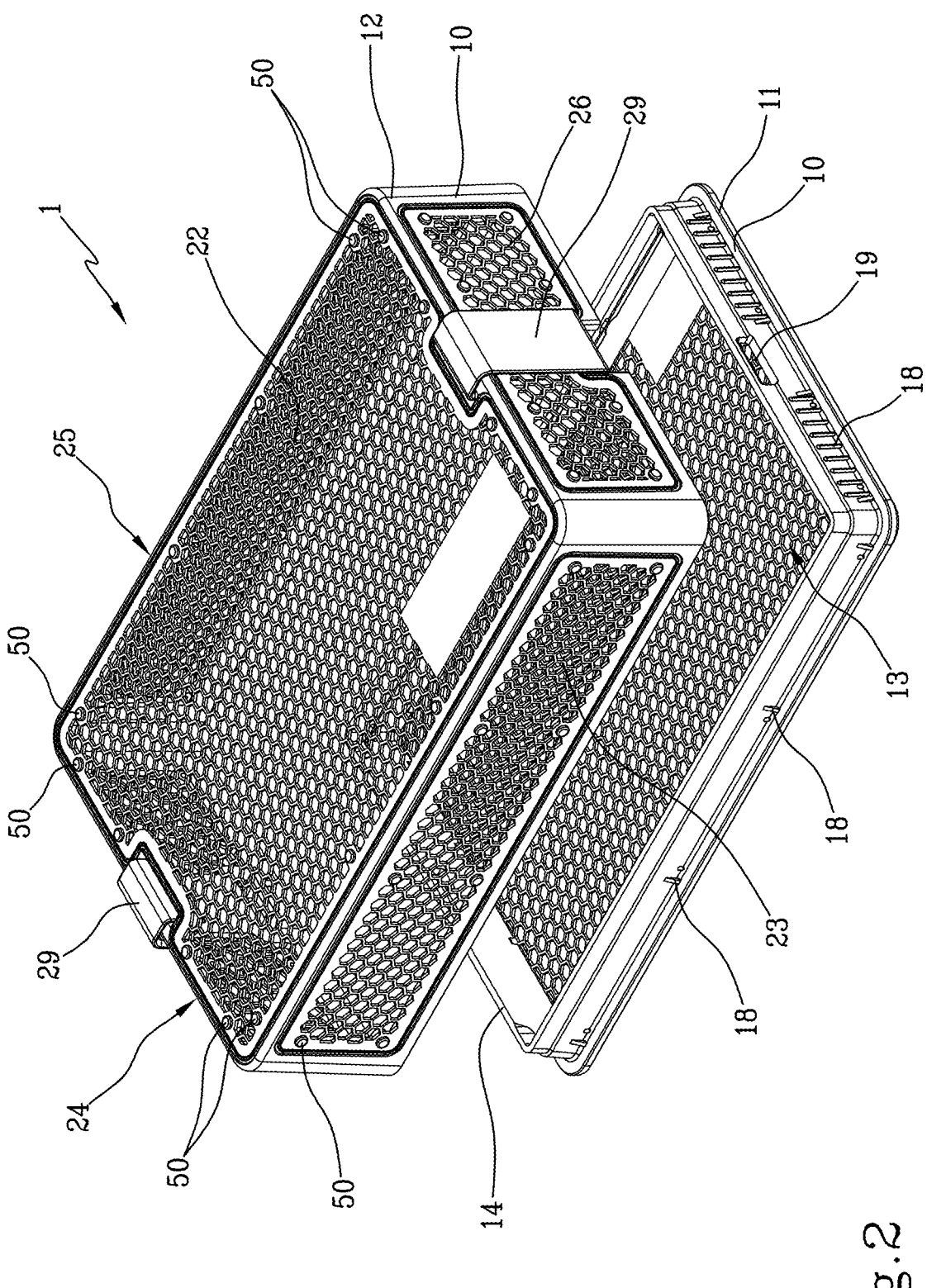
FIG. 2 shows a schematic view of the embodiment of the container of FIG. 1 in an opening configuration.
Figure 4:
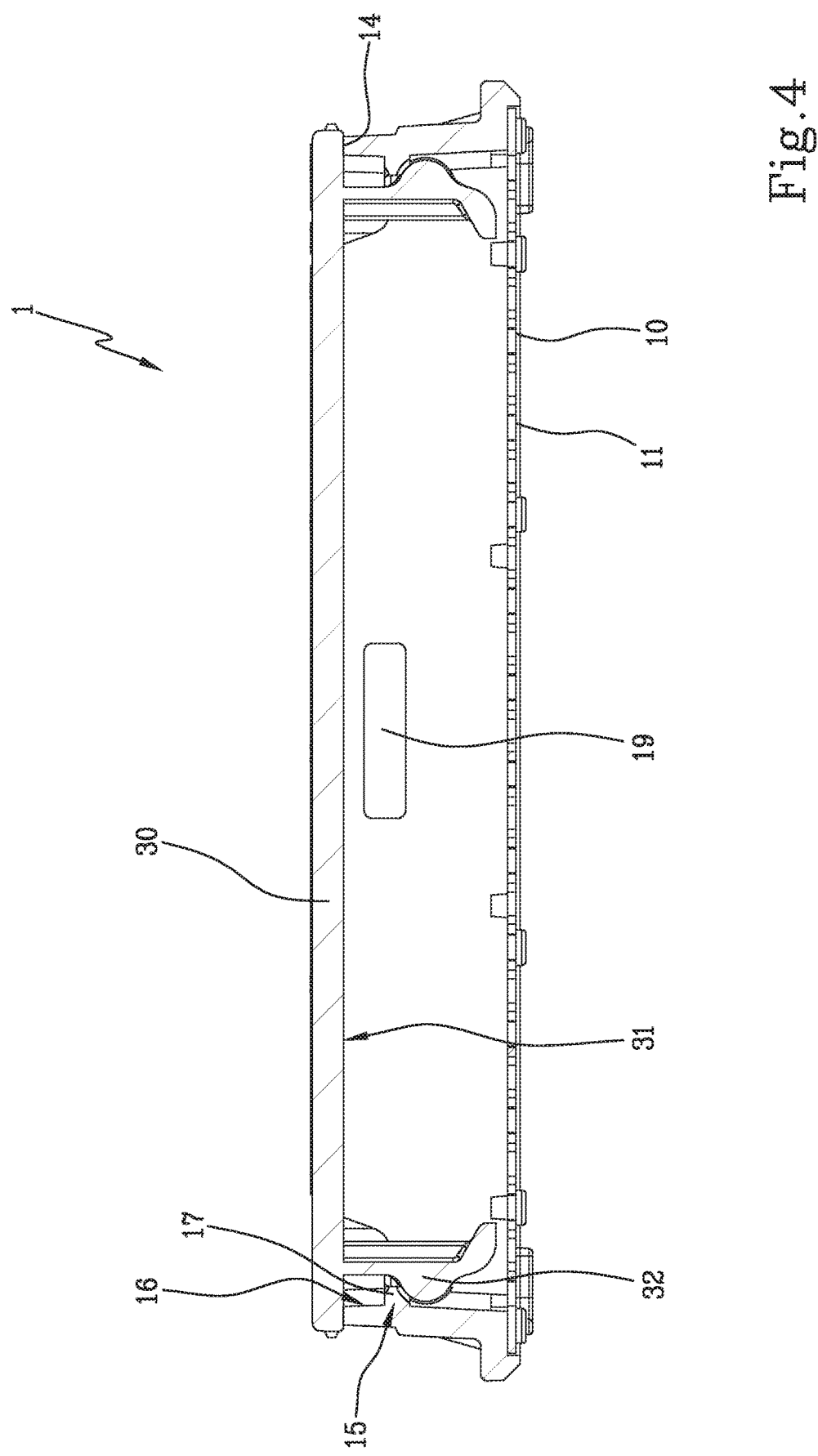
FIG. 4 shows a schematic sectional view of the embodiment of the container of FIG. 1 without the covering element.

Preferably, as can be seen in FIGS. 2, 3 and 4, the base element 11 has guide recesses and/or guide protrusions engageable to guide protrusions and/or guide recesses of the covering element 12.

Advantageously, such a feature allows to precisely align the base element 11 to the covering element 12 during the closing step of the container 1. Furthermore, such guide elements 18 allow to improve and stabilise the closing configuration of the container 1.

According to a further aspect of the present invention, the housing seat 13 is arranged at a first height while the bottom wall 21 is arranged at a second height, different from the first height, so that, in use, a lower surface 31 of the one or more instrument support trays 30 is spaced from the bottom wall 21 of the container 1.

That is, in use, the one or more instrument support trays 30 are arranged in a raised position and spaced apart with respect to the bottom wall 21. Advantageously, it is thereby possible to more efficiently exploit the space of the containment volume "V". In fact, since the one or more instrument support trays(s) 30, in use, are distanced from the bottom wall 21, it is possible to insert further medical instruments between the lower surface 31 of the instrument support tray 30 and the bottom wall 21 of the container 1.

In this regard, the kit can also comprise one or more instrument clippers, not illustrated in the appended drawings, which can be reversibly attached to the container 1, preferably to the bottom wall 21.

Advantageously, by exploiting the one or more instrument support trays 30 together with the instrument clippers, it is thereby possible to insert a greater amount of medical instruments in the container 1 so as to efficiently exploit the containment volume "V" of the container 1.

According to the preferred embodiment, illustrated by way of example in the appended drawings, the housing seat 13 is defined by an upper edge 14 of the base element 11. Such an upper edge 14 is adapted to restingly receive the one or more instrument support trays 30.

Preferably, moreover, the upper edge 13 defines a rest surface substantially parallel to the bottom wall 21. It follows that, in use, also the one or more instrument support trays 30 are substantially parallel to the bottom wall 21 and mutually coplanar.

Figure 5A:
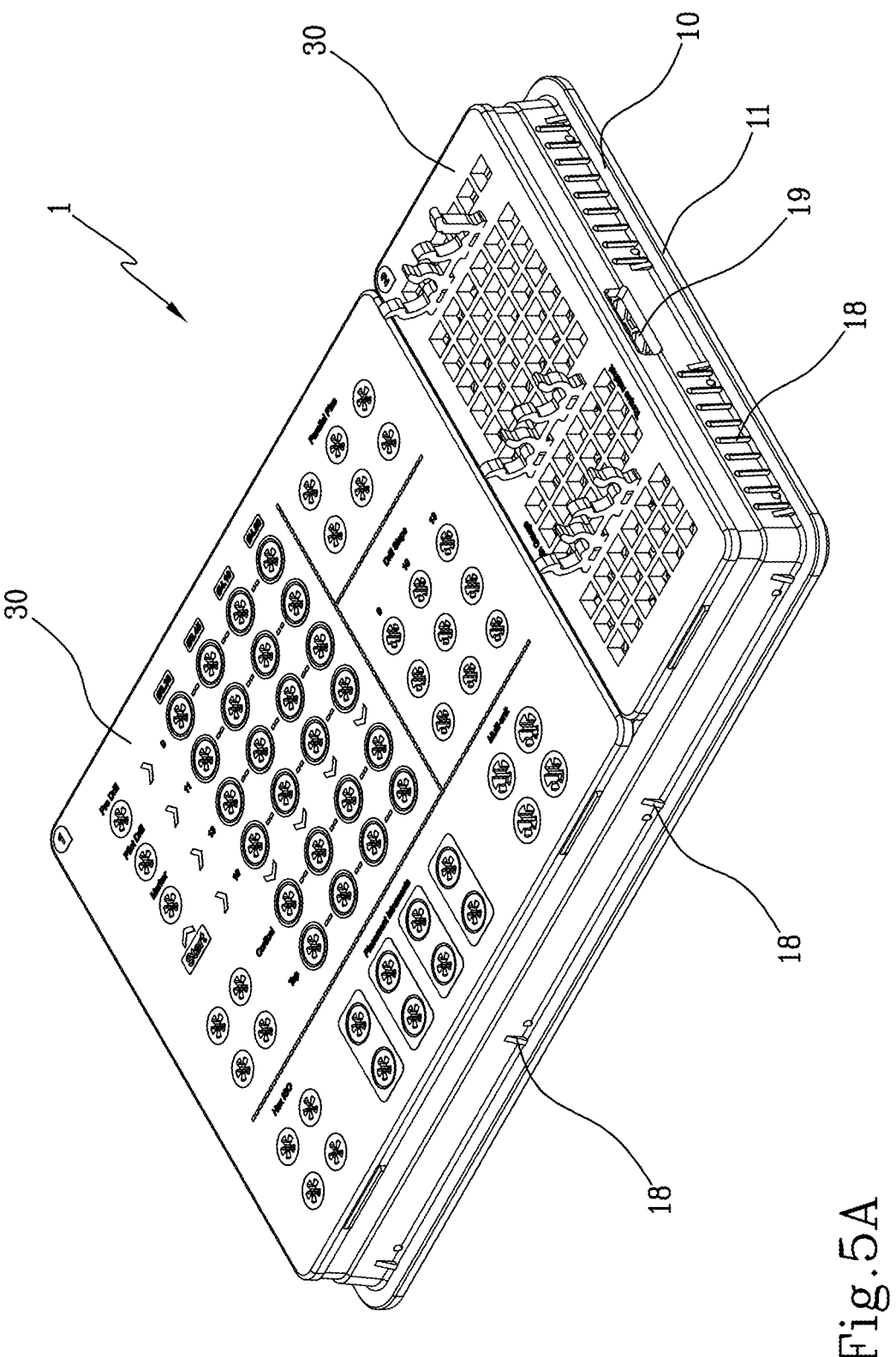
FIGS. 5A-5B show different embodiments of the kit in accordance with the present invention.
Figure 5B:
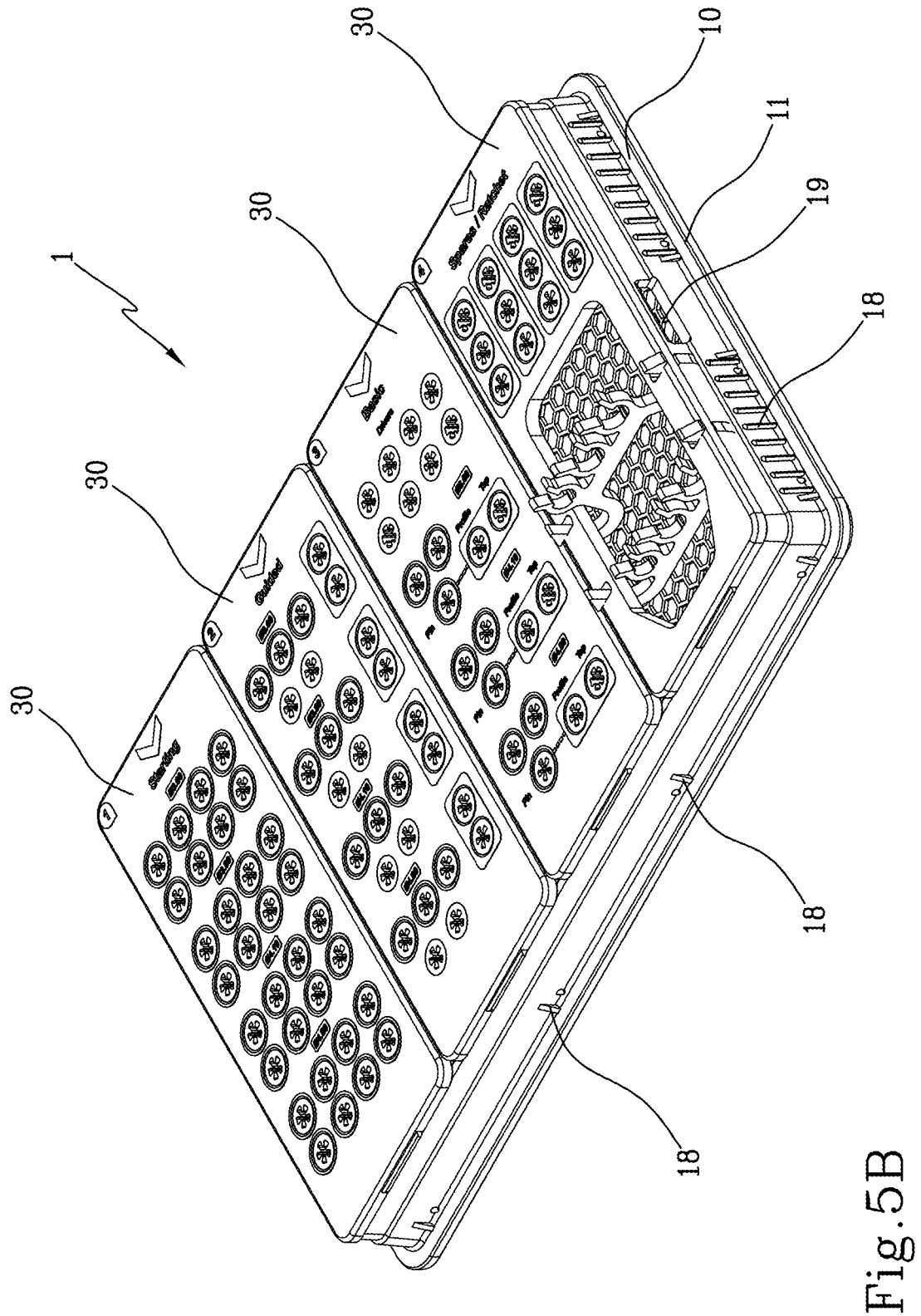

According to a further aspect of the present invention, the one or more instrument support trays 30 are arranged to be mutually connectable to the container 1 in accordance with a plurality of different configurations and combinations so that the kit, in use, can overall assume a plurality of distinct operating compositions, as illustrated for example in FIGS. 5A and 5B. That is, instrument support trays 30 are arranged to be mutually connectable to said container 1, and in particular to the housing seat 13, in a modular manner.

Said container 1 and said housing seat 13 are configured and shaped to contain said instrument support trays 30 in a modular manner in accordance with a plurality of different configurations and combinations thereof so that the overall planar surface of said one or more instrument support trays 30 is the same or less than said housing seat 13. Still in other words, the upper edge defining said rest surface is counter-shaped to the edge of the trays 30 so as to be able to support them in a modular manner. Furthermore, the upper edge defining said rest surface is counter-dimensioned to the edge of the trays 30 so as to be able to support them in a modular manner.

In fact, the kit can comprise one or two or more instrument support trays 30 having respective plan surfaces of different sizes.

Advantageously, the kit is thereby extremely versatile and adaptable to a plurality of operating conditions.

Regardless of the number and planar size of the instrument support trays 30, the overall plan surface of the one or more instrument support trays 30 must be the same or less than the housing seat 13.

Preferably, in order to use the entire available surface of the housing seat 13, the one or more instrument support trays 30 define a substantially continuous plane aligned with the upper edge 14 of the base element 11, as illustrated in FIGS. 5a and 5B.

Alternatively, it is possible to arrange the instrument support trays 30 in number and size such as to only partially utilise the available surface of the housing seat 13.

As illustrated by way of example in FIG. 4, according to a further aspect of the present invention, the base element 11 can have anchoring portions 15 reversibly engageable to respective anchoring elements 32 of the one or more instrument support trays 30 so as to define a stable attachment of the one or more instrument support trays 30 to the base element 11.

That is, the one or more instrument support trays 30 can have anchoring elements 32, attached to the one or more instrument support trays 30 or made integrally with the one or more instrument support trays 30, configured to reversibly engage the anchoring portions 15 of the container 1.

Advantageously, such a technical feature allows to define a stable anchoring of the one or more instrument support trays 30 to the base element 11 so as to more easily mount the kit during the pre-washing step and to make the one or more instrument support trays 30 more stable inside the container 1 during the washing itself.

In particular, the base element 11 can have a pair of inner side walls 16 opposite to each other, each provided with protrusions and/or recesses defining the anchoring portions 15.

Preferably, the anchoring seats 19 are made on a pair of side walls 16 which are distinct with respect to the side walls 16 on which the above-mentioned protrusions and/or recesses are made.

In turn, the anchoring elements 32 can extend away from the lower surface 31 of the one or more instrument support trays 30. Such a feature allows the anchoring elements 32 to be reversibly constrained to the protrusions and/or recesses of the inner side walls 16 of the base element 11.

In the preferred embodiment, illustrated by way of non-limiting example in the appended drawings, the protrusions and/or recesses of the base element 11 comprise an anchoring tab 17, attached or integral with the respective inner side wall 16. Structurally, each tab 17 extends away from the respective inner side wall 16, preferably transversely thereto, and extends at least partially, preferably entirely, along a width of the respective inner side wall 16.

That is, each tab 17 is parallel to the bottom wall 21 and therefore parallel to the upper edge 14.

The anchoring elements 32 of the one or more instrument support trays 30 are elastically deformable and preferably configured to define a snap coupling with the anchoring portions 15, and in particular with the tabs 17.

Advantageously, in use, such an embodiment allows a translation of the one or more instrument support trays 30 mounted on the base element 11. According to a further aspect of the present invention, the one or more instrument support trays 30 can be made of a polymeric material. Similarly, the anchoring elements 32, preferably integral with the respective instrument support tray 30, can also be made of a polymeric material, and preferably of the same material as the respective instrument support tray.

Preferably, the instrument support trays 30 are made of a rigid polymeric material, preferably PPSU. Similarly, the instrument clippers can also be made of a rigid polymeric material (PPSU), but are in any case capable of bending to allow the coupling/uncoupling operations.

The fact that the instrument support trays 30 are made of rigid polymeric material is particularly advantageous if the kit is used in an ultrasonic type cleaner, but also for normal washing. In fact, the rigidity of the material used allows the instrument support trays 30 and/or the instrument clippers to not absorb the ultrasound (unlike silicone that would tend to absorb it), allowing a deep and optimal cleaning of the medical instruments thereto. Finally, it should be noted that the entire container is made of plastic material, preferably PPSU, with the exception of the containment panels 20 which are made of metal material.

The present invention achieves the intended objects, eliminating the drawbacks highlighted by the prior art: in this regard, it should firstly be noted that the container 1 as described and/or claimed allows to significantly reduce production burdens, in terms of costs and time.

It should also be noted that the kit as described and/or claimed allows a wide versatility of use as well as a high efficiency in the cleaning and sterilising of medical instruments. Not least, the kit as described and/or claimed is easily usable.

The invention claimed is:

1. A kit for washing and/or disinfecting and/or sterilising medical instruments, comprising:
   a container for washing and/or disinfecting and/or sterilising medical instruments;
   one or more instrument support trays of substantially planar shape, having a polygonal plan shape and having a plurality of retaining seats for said instruments;
   said container comprising:
   a frame, made of a polymeric material and defining a containment volume, said frame comprising a base element, adapted to define a housing seat for said one or more instrument support trays, and a covering element that can be reversibly coupled to said base element using a coupling mechanism, the covering element configured to at least partially cover said base element when said container is in a closing configuration, wherein said base element comprises lateral walls, wherein the lateral walls comprises a support edge located on a side of a given of the lateral walls facing an interior portion of the container, wherein the lateral walls comprise at least one anchoring portion;
   a plurality of containment panels, comprising a metal material, constrainable to said frame, the plurality of containment panels defining a bottom wall, an upper wall, and a plurality of side walls of said container and delimiting said containment volume, said containment panels comprising a plurality of holes, said plurality of containment panels having a planar shape;
   wherein said one or more instrument support trays are arranged to be mutually connectable to said container in a modular manner in accordance with a plurality of different configurations, wherein said one or more instrument support trays comprise at least one anchoring element extending below a bottom surface of a given of the one or more instrument support trays, wherein the at least one anchoring element is reversibly engageable with the at least one anchoring portion of the base element.

2. The kit according to claim 1, wherein said housing seat is arranged at a first height and wherein said bottom wall is arranged at a second height, different from the first height, so that, in use, a lower surface of said one or more instrument support trays is spaced from said bottom wall of said container.

3. The kit according to claim 1, wherein said housing seat is defined by an upper edge of said base element adapted to restingly receive said one or more instrument support trays, preferably said upper edge defining a rest surface substantially parallel to said bottom wall.

4. The kit according to claim 1, wherein said anchoring portions when engaged with respective anchoring elements of said one or more instrument support trays provide a stable attachment of said one or more instrument support trays to said base element.

5. The kit according to claim 4, wherein said base element has a pair of inner side walls opposite to each other, each provided with protrusions and/or recesses defining said anchoring portions.

6. The kit according to claim 5, wherein said protrusions and/or recesses comprise an anchoring tab, attached to or integral with the respective inner side wall, extending away from the respective inner side wall and extending at least partially along a width of the respective inner side wall.

7. The kit according to claim 1, wherein said base element and said covering element comprise guide elements counter-shaped to each other and adapted to define a unique mutual positioning between said base element and said covering element in said closing configuration of said container.

8. The kit according to claim 1, wherein said base element and said covering element comprise reversible mutual coupling means configured to determine a stable attachment of said base element to said covering element.

9. The kit according to claim 4, wherein said one or more instrument support trays have anchoring elements attached to said one or more instrument support trays or made integrally with said one or more instrument support trays, configured to reversibly engage to said anchoring portions of said container.

10. The kit according to claim 9, wherein said one or more instrument support trays are made of a polymeric material and wherein said anchoring elements are elastically deformable.

11. The kit according to claim 10, comprising two or more instrument support trays having respective plan surfaces of different sizes.

12. A container for washing and/or disinfecting and/or sterilising medical instruments comprising:
   a frame, made of a polymeric material and defining a containment volume, said frame comprising a base element, adapted to define a housing seat for one or more instrument support trays, and a covering element, the covering element being reversibly couplable to said base element using a coupling mechanism and configured to at least partially cover said base element when said container is in a closing configuration, wherein said base element comprises lateral walls, wherein the lateral walls comprises a support edge located on a side of a given of the lateral walls facing an interior portion of the container, wherein the lateral walls comprise at least one anchoring portion;
   a plurality of containment panels, comprising a metal material, constrainable to said frame, the plurality of containment panels defining a bottom wall, an upper wall, and a plurality of side walls of said container and delimiting said containment volume, said containment panels comprising a plurality of holes, said plurality of containment panels having a planar shape;
   wherein said container and said housing seat are shaped to contain said instrument support trays in a modular manner in accordance with a plurality of different configurations, wherein said one or more instrument support trays comprise at least one anchoring element extending below a bottom surface of a given of the one or more instrument support trays, wherein the at least one anchoring element is reversibly engageable with the at least one anchoring portion of the base element.

* * * * *